United States Patent [19]

Duffett et al.

[11] Patent Number: Plant 5,447

[45] Date of Patent: Apr. 23, 1985

[54] CHRYSANTHEMUM PLANT NAMED REMARKABLE

[75] Inventors: William E. Duffett, Salinas, Calif.; Grace H. Mack, 108 Wahackme Rd., New Canaan, Conn. 06840

[73] Assignee: Grace H. Mack, New Canaan, Conn.

[21] Appl. No.: 514,319

[22] Filed: Jul. 15, 1983

[51] Int. Cl.[3] ..... A01H 5/00

[52] U.S. Cl. ..... Plt./82

[58] Field of Search ..... Plt./82

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum cultivar named Remarkable, identified by the combined characteristics of flat capitulum form, decorative capitulum type, orange-red floret color, diameter across face of capitulum up to 50 mm., short plant height, semi-spreading branching pattern, average natural season flowering date of September 20, and average flowering response period of seven weeks in photoperiodic controlled short day programs with excellent adaptability and performance in April - May pot mum flowerings.

3 Drawing Figures

The present invention comprises a new and distinct cultivar of *Chrysanthemum morifolium,* Ramat., named Remarkable.

Remarkable is a product of a planned breeding program which had the objective of creating cultivars with decorative capitulum type, short height, spreading branching pattern, durable infloresence, 6 to 7 week flowering response period, and bronze ray floret color under outdoor natural season environments.

Remarkable was originated from a cross made by Grace H. Mack in a controlled breeding program in New Canaan, Conn. in the year 1978. The female parent was the bronze red pompon Bandit disclosed in U.S. Plant Pat. No. 4,491. The male parent was an unnamed bronze decorative seedling identified as 78 MOO-3.

Remarkable was discovered and selected as a flowering plant within the progeny of the stated cross by William E. Duffett on Oct. 5, 1979 in an outdoor field in Salinas, Calif. The first act of asexual reproduction for Remarkable was accomplished when vegetative cuttings were taken from the initial selection in February 1980 under procedures formulated and supervised by William E. Duffett. Horticultural examination of selected units initiated June 1980 has demonstrated that the combination of characteristics herein disclosed for Remarkable are firmly fixed and are retained through successive generations of asexual reproduction.

Remarkable has not been observed under all possible environmental conditions. The phenotype may vary significantly with variations in environment such as temperature, light intensity, and day length. The following observations, measurements, and comparisons describe plants grown in a field in Salinas, Calif.

Rooted cuttings were established in soil in one gallon containers maintained outdoors under the natural temperature and day length prevailing during July through September. Single pinching was practiced with all branches and buds retained.

The following traits have been repeatedly observed and are determined to be basic characteristics of Remarkable which in combination distinguish this chrysanthemum as a new and distinct cultivar:

(1) Flat capitulum form.

(2) Decorative capitulum type.

(3) Orange-red ray floret color.

(4) Diameter across face of capitulum up to 50 mm.

(5) Short plant height.

(6) Semi-spreading branching pattern.

(7) Average natural season flowering date of September 20.

(8) Average flowering response period of seven weeks in photoperiodic controlled short day programs with excellent adaptability and performance in April - May pot mum flowerings.

The accompanying photographic drawings show typical inflorescence and foliage characteristics of Remarkable. Sheet 1 is a color photograph of Remarkable. Sheet 2 is a black and white photograph showing three views of the inflorescence of Remarkable. Sheet 3 is a black and white photograph showing the leaves of Remarkable at three stages of development (mature, intermediate, immature).

Of the many commercially available cultivars known to the present inventors, the most similar existing cultivars in comparison to Remarkable are Minnautumn, unpatented and commercially available, and Zest, disclosed in U.S. Plant Pat. No. 4,227.

Reference is made to the attached Chart A which compares certain characteristics of Remarkable with the same characteristics of Minnautumn and Zest. It will be noted that in comparison to Minnautumn and Zest, Remarkable has a more intense orange-red color, compared to the bronze-red color of the comparison cultivars. Minnautumn has the largest diameter across face of capitulum and a more spreading plant habit. Zest has the most rapid response in spring pots and natural season flowering. The three varieties are similar in capitulum type, form and plant height.

In the following description, color references are made to The Royal Horticultural Society Colour Chart. The color values were determined between 10:30 and 11:00 AM on Sept. 18, 1982 and May 12, 1983 under 150 foot-candle light intensity at Salinas, Calif.

Bontanical classification:*Chrysanthemum morifolium,* Ramat., cv Remarkable.

INFLORESCENCE

Capitulum:

*Form.*—Flat.

*Type.*—Decorative.

*Permanence.*—Durable up to three weeks. Resists shatter.

*Diameter across face.*—Up to 50 mm.

Corolla of ray florets: Orange-red.

*Color (abaxial).*—34A-C.

*Color (adaxial).*—34D.

Reproductive organs:

*Androecium.*—Present disc florets; pollen moderate.

*Gynoecium.*—Present both ray and disc florets.

Corolla of disc florets:

*Color.*—Immature — 2A. Mature — 12A.

PLANT

General appearance: Short, compact, strong, semi-spreading habit.

Foliage:

*Color (abaxial).*—147A.

*Color (Adaxial).*—147B.

Shape: Deeply lobed. Deeply serrated.

CHART A

COMPARISON OF REMARKABLE, MINNAUTUMN AND ZEST

| CULTIVAR | RAY FLORET COLOR | CAPITULUM FORM AND TYPE | AVERAGE NATURAL SEASON FLOWER DATE | PLANT HEIGHT |
|---|---|---|---|---|
| REMARKABLE | ORANGE RED | FLAT DECORATIVE | SEPTEMBER 20 | SHORT |
| MINNAUTUMN | BRONZE RED | FLAT DECORATIVE | SEPTEMBER 25 | SHORT |
| ZEST | BRONZE RED | FLAT DECORATIVE | SEPTEMBER 15 | SHORT |

CHART A-continued

COMPARISON OF REMARKABLE, MINNAUTUMN AND ZEST

| CULTIVAR | BRANCHING PATTERN AND SPREAD | DIAMETER ACROSS FACE OF CAPITULUM | PERMANENCE OF FORM & COLOR |
|---|---|---|---|
| REMARKABLE | SEMI SPREADING | 50 mm. | UP TO 3 WEEKS |
| MINNAUTUMN | SPREADING | 60 mm. | UP TO 2 WEEKS |
| ZEST | UPRIGHT | 50 mm. | UP TO 3 WEEKS |

COMPARISONS MADE OF PLANTS GROWN UNDER NATURAL SEASON OUTDOOR FIELD CONDITIONS IN SALINAS, CALIFORNIA.

We claim:

1. A new and distinct cultivar of *Chrysanthemum morifolium,* Ramat., plant named Remarkable, as described and illustrated, and identified by the combined charcteristics of flat capitulum form, decorative capitulum type, orange-red ray floret color, diameter across face of capitulum up to 50 mm., short plant height, semi-spreading branching pattern, average natural season flowering date of September 20 and average flowering response period of seven weeks in photoperiodic controlled short day programs.

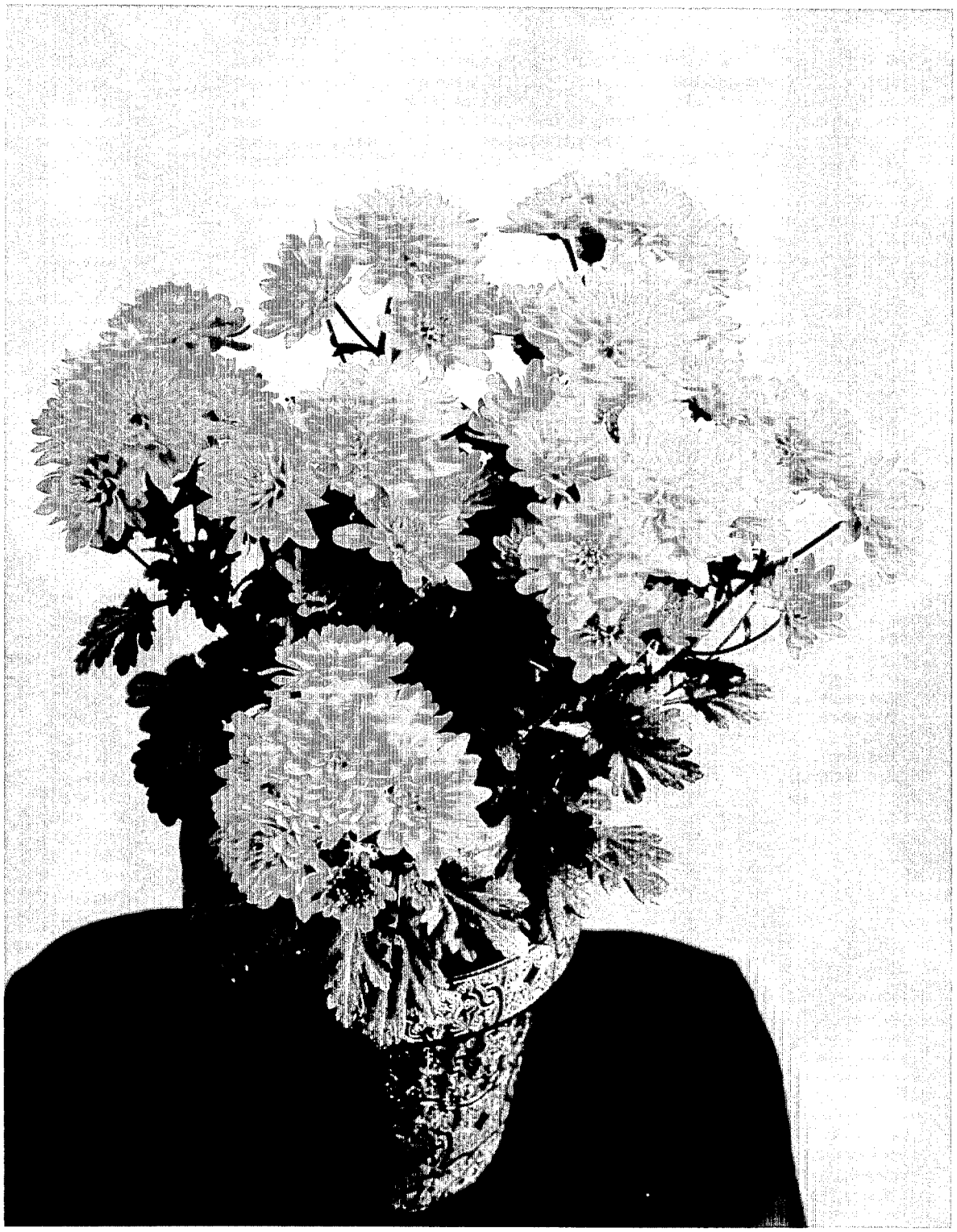

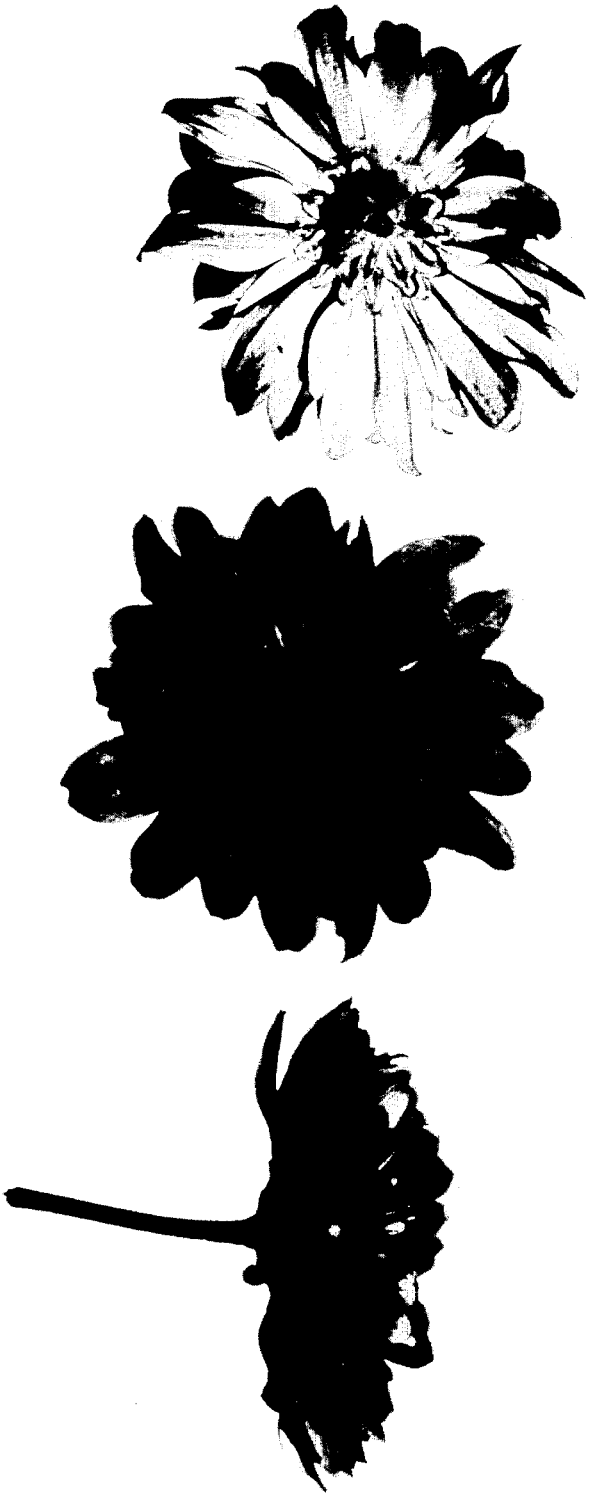

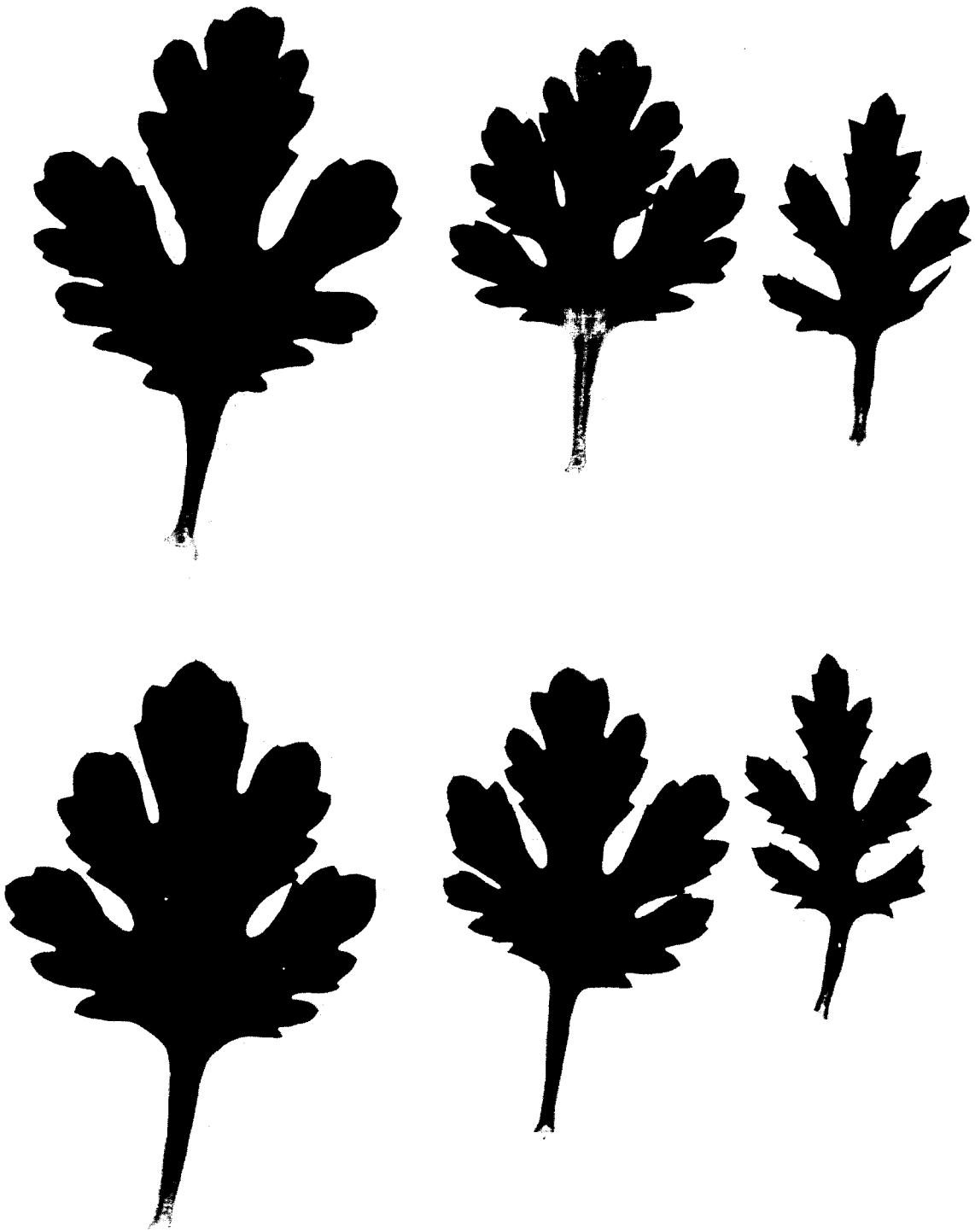

* * * * *